United States Patent [19]
Cooper et al.

[11] Patent Number: 6,017,894
[45] Date of Patent: Jan. 25, 2000

[54] *ACTINOMADURA FULVA* SUBSP *URUGUAYENSIS* AND ANTIMICROBIAL COMPLEX AND ANTIMICROBIAL COMPOUNDS ISOLATED THEREFROM

[75] Inventors: Raymond Cooper, E. Brunswick; Ann C. Horan, Summit; Mahesh G. Patel, Verona; Imbi Truumees, Cresskill; Raymond F. Yarborough, Orange, all of N.J.

[73] Assignee: Schering Corporation, Kenilworth, N.J.

[21] Appl. No.: 07/746,050

[22] Filed: Aug. 12, 1991

Related U.S. Application Data

[63] Continuation of application No. 07/590,570, Sep. 28, 1990, abandoned, which is a continuation of application No. 07/227,964, Aug. 3, 1988, abandoned.

[51] Int. Cl.$^7$ ............................ A61K 31/71; C07H 17/00
[52] U.S. Cl. ......................... 514/29; 536/17.4; 536/18.7; 435/75; 435/825
[58] Field of Search ................ 514/29; 536/17.4, 536/18.7; 435/75, 825

[56] References Cited

U.S. PATENT DOCUMENTS 4,517,359   5/1985   Kobrehel et al. .................. 536/7.4

FOREIGN PATENT DOCUMENTS 18035   4/1984   Japan .

*Primary Examiner*—Elli Peselev
*Attorney, Agent, or Firm*—Thomas D. Hoffman

[57] ABSTRACT

Three novel macrolactam monosaccharides isolated from an antimicrobial complex 510 produced in fermentation under controlled conditions using a biologically pure culture of the microorganism *Actinomadura fulva* subsp. *uruguayensis* ATCC 53713.

12 Claims, No Drawings

ACTINOMADURA FULVA SUBSP URUGUAYENSIS AND ANTIMICROBIAL COMPLEX AND ANTIMICROBIAL COMPOUNDS ISOLATED THEREFROM

This is a continuation of application Ser. No. 07/590,570 filed Sep. 28, 1990 now abandoned which is a continuation of application Ser. No. 227,964 filed Aug. 3, 1988 now abandoned.

This invention relates to three novel macrolactam monosaccharide antimicrobial compounds. The compounds are isolated from an antimicrobial complex 510 which is produced in fermentation under controlled conditions using a biologically pure culture of the microorganism, *Actinomadura fulva* subsp. *uruguayensis* SCC 1778, ATCC 53713.

CROSS REFERENCE TO RELATED APPLICATIONS

In a related, commonly assigned, co-pending application Ser. No. 07/227,963 (Attorney's Docket No. 2516), filed on the same date as this application, a novel macrolactam disaccharide produced by fermentation of *A. fulva* subsp. *indica* ATCC 53714 is disclosed.

In another related, commonly-assigned, U.S. Pat. No. 5,837,691, based on Ser. No. 747,456, filed Aug. 12, 1991 which is a continuation of Ser. No. 590,314, filed Sep. 28, 1990, abandoned, which is a continuation of Ser. No. 227,968, abandoned (Attorney's Docket No. 2517) filed on the same date as this application, a novel macrolactam monosaccharide produced by fermentation of *A. vulgaris* subsp. *vulgaris* sp. nov., ATCC 53748 are disclosed.

In another related, commonly-assigned co-pending application Ser. No. 07/227,951 (Attorney's Docket No. 2519), filed on the same date as this application, a novel macrolactam monosaccharide produced by fermentation of *A. vulgaris* subsp. *lanata* ATCC 53715 is disclosed.

SUMMARY OF THE INVENTION

The present invention embraces *Actinomadura fulva* subsp. *uruguayensis* SCC 1778, ATCC 53713 and mutants and variants thereof having the identifying characteristics of *Actinomadura fulva* subsp. *uruguayensis*

Another aspect of the present invention is directed to the antimicrobial complex 510 produced by cultivating a strain of *Actinomadura fulva* subsp. *uruguayensis* SCC 1778 having the identifying characteristics of ATCC 53713 in a pH and temperature controlled medium having assimilable sources of carbon and nitrogen under controlled submerged aerobic conditions until a composition of matter having substantial antimicrobial activity is produced.

The present invention is also directed to three components of the antimicrobial complex 510, i.e. the compounds represented by the formula 1:

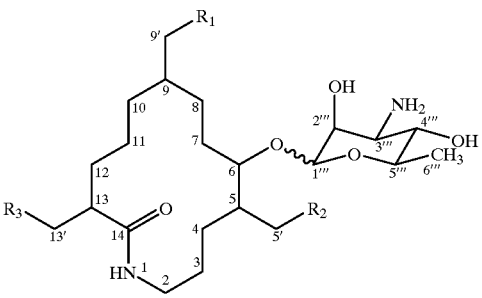

wherein $R_1=R_2=R_3=H$; or $R_1=R_2=H$ and $R_3=CH_3$; or $R_1=H$ and $R_2=R_3=CH_3$;
in substantially chemically pure form,
or a pharmaceutically acceptable salt thereof.

THE MICROORGANISM

The microorganism used for the production of antimicrobial complex 510 and the compound represented by formula 1 is a biologically pure culture of *Actinomadura fulva* subsp. *uruguayensis* subsp. nov. Shearer, Brodsky and Horan SCC 1778, ATCC 53713.

A viable culture of this microorganism has been deposited under the provisions of the Budapest Treaty in the collection of the American Type Culture Collection (ATCC) to 10801 University Boulevard, Manassas, Va. 20110-2209, where it has been assigned accession number ATCC 53713. Should the deposited culture become lost, destroyed or non-viable during the longer of the thirty (30) year period from the date the culture was deposited or the five (5) year period after the last request for the deposited culture or the effective life of the patent which issues from this application, the culture will be replaced upon notice by applicants or assignee(s) of this application. Subcultures of *Actinomadura fulva* subsp. *uruguayensis* SCC 1778, ATCC 53713 are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the US Patent Laws.

The microorganism was isolated from a sample of soil collected in Uruguay. It had been characterized and found to have the microscopic, macroscopic, and whole cell hydrolysis properties of the genus Actinomadura.

DESCRIPTION OF THE PRODUCING STRAIN: ACTINOMADURA FULVA SUBSP. URUGUAYENSIS SCC 1778, ATCC 53713

Source material for the following taxonomic evaluations was a frozen preparation of a pure culture of *Actinomadura fulva* subsp. *uruguayensis* SCC 1778, ATCC 53713. Inoculum for the biochemical and physiological tests was prepared according to the procedures of Horan and Brodsky [Horan and Brodsky, *Int. J. Syst. Bacteriol.*, Vol. 32, pp. 195–200 (1982)]. The incubation temperature for the biochemical and physiological tests was 30° C. Readings of the results were made at various times up to 21 days for the plate media. Most of the tubed media were read at various times up to 28 days. The tests for decomposition of urea, allantoin and hippurate, as well as the tests for the reduction of nitrates were read for six weeks.

MORPHOLOGY

Morphological observations of the producing strain of the microorganism of this invention were made on plates of water agar, AV-agar [Nonomura and Ohara, *J. Ferment. Technol.*, Vol. 47, pp. 463–469 (1966)] or modified inorganic salts-starch agar [Difco inorganic salts-starch agar (ISP-4), 12 g; Difco Bacto agar, 15 g; distilled water, 800 ml; soil extract 200 ml; thiamine HCL, 0.5 mg; riboflavin, 0.5 mg; niacin, 0.5 mg; pyridoxine HCL, 0.5 mg; inositol, 0.5 mg; calcium pantothenate, 0.5 mg; p-aminobenzoic acid, 0.5 mg; biotin, 0.25 mg]. Plates were incubated at 30° C. and observed for 4 to 6 weeks.

*A. fulva* subsp. *uruguayensis* is a gram positive, filamentous organism that forms a mycelium differentiated into: (1) a substrate mycelium that penetrates the agar and forms a compact surface layer, and (2) an aerial mycelium that originates from the substrate mycelium.

The substrate mycelium is well developed with moderately branching, non-fragmenting hyphae which are approximately 0.4 μm to 0.8 μm in diameter. No spores are observed on the substrate hyphae.

The aerial hyphae, which are approximately 0.6 μm to 1.0 μm in diameter, bear chains of spores. These spore chains contain approximately 6 to 23 spores per chain. The smooth walled spores are round to ovoid and approximately 1.1 to 1.5 μm in diameter. The spore chains are arranged in tightly appressed spirals, forming pseudosporangia approximately 1.5 to 5.5 μm in diameter. No motile elements are observed in either the substrate or aerial mycelium.

CHEMOTAXONOMY

Purified cell wall preparations of the producing strain of this invention were analyzed by the method of Becker [Becker et. al., *Appl, Microbiol.*, Vol. 12, pp. 421–423 (1964)] and shown to contain the meso-isomer of 2,6-diaminopimelic acid, alanine, glutamic acid, glucosamine, muramic acid and traces of mannose. Whole-cell hydroysates were analyzed by the method of Lechevalier [Lechevalier, M. P., *J. Lab. Clin. Med.*, Vol. 71, pp. 934–944 (1968)] and shown to contain glucose, mannose, madurose, ribose, a trace of galactose and a trace of rhamnose. The phospholipids present are diphosphatidylglycerol, phosphatidylinositol, phosphatidylethanolamine and unknown glucosamine-containing phospholipids. Thus, the producing strain of the microorganism of this invention, SCC 1778, has a type III cell wall with a type B whole-cell sugar pattern and a type P IV phospholipid composition [Lechevalier et. al., *Biochem. System. Ecol.*, Vol. 5, pp. 249–260 (1977)], typical of actinomadurae.

PHYSIOLOGICAL AND BIOCHEMICAL CHARACTERISTICS

The procedures used were those cited by Gordon [Gordon, R. E., *J. Gen. Microbiol.*, Vol. 45, pp. 355–364 (1966)], Luedemann and Brodsky [Luedemann and Brodsky, "*Antimicrob. Agents Chemother.*" pp 47–52 (1965)] and Horan and Brodsky [Horan and Brodsky, *Int. J. Syst. Bacteriol.*, Vol. 32, pp. 195–200 (1982)]. The producing strain, *A. fulva* subsp. *uruguayensis*, SCC 1778, produces acid from adonitol, D-arabinose, D-fructose, L-fucose, D-galactose, glucose, glycerol, i-inositol, maltose, D-mannitol, D-mannose, α-D-melibiose, α-methyl-D-glucoside, β-methyl-D-glucopyranoside, α-L-rhamnose, D-ribose, sucrose, D-treholose and D-xylose but not from L-arabinose, dulcitol, i-erythritol, D-melizitose, or D-sorbitol. Adenine, hypoxanthine, L-tyrosine, elastin and casein are hydrolyzed but guanine, xanthine, xylan hippurate and chitin are not. Gelatin is both hydrolyzed and liquified. Starch hydrolysis is negative. Urease and allantoinase are not formed. Nitrate is reduced to nitrite. Melanin and hydrogen sulfide are not formed. Growth does not occur at 10° C. or at 45° C. Growth is fair at 40° C. The microorganism of this invention, SCC 1778, grows in the presence of 3% NaCl but grows poorly to fairly at 4% NaCl solution. Acetate, butyrate, lactate, pyruvate and succinate are utilized; benzoate, formate, oxalate and tartrate are not.

*A. fulva* subsp. *uruguayensis* grows in the presence of 50 μg/ml of streptomycin, kanamycin, novobiocin, rifamycin, erythromycin, penicillin G, cephalothin, tetracycline, cycloserine and spectinomycin and in the presence of 10 mcg/ml of neomycin. Growth is poor in the presence of 50 mcg/ml of sisomicin, gentamicin and clindamycin.

DESCRIPTION OF *A. FULVA* SUBSP. *URUGUAYENSIS* ON VARIOUS MEDIA

All plates were incubated at 30° C. and observed at intervals up to 28 days. The common names for the colors were choosen after comparison with color chips from the ISCC-NBS centroid color charts, the "*Color Harmony Manual*", Ed. 4 (Container Corp. America, 1958), or the "*Methuen Handbook of Color*" (Eyre Methuen, London, 1981). On all media tested, the substrate mycelium of *A. fulva* subsp. *uruguayensis* is off-white, yellow-brown or brown. Few aerial mycelia are produced by SCC 1778 but when visible, the aerial mycelia are white to ivory to yellowish-gray. Yellow-brown diffusible pigments are produced. Characteristics are presented in Table 1.

On the basis of its morphological and chemotaxonomic characteristics, the producing strain of of this invention, SCC 1778, was placed in the genus Actinomadura. The description of the microorganism of this invention, SCC 1778, was compared to the descriptions of Actinomadura species found on the approved lists of bacterial names or in the patent literature. The microorganism of this invention, SCC 1778, was found to resemble the descriptions of *Actinomadura fulva* and was therefore compared to *A. fulva* Ferm-P3683 disclosed by A. Tamura and A. Tanaka (Dainippon) in Japanese Patent Publication No. 18035, published Apr. 25, 1984, based on Japanese Kokai 78-28, 101, published Mar. 16, 1978 as well as *A. fulva* subsp. *indica* SCC 1840, ATCC 53714 disclosed in commonly-owned, co-pending application (Attorney's Docket No. 2516).

All three cultures are similar in morphology and growth characteristics on various media. All form a substrate mycelium which varies from off-white through yellow to yellow-brown and brown. The Japanese Patent discloses that *A. fulva* Ferm P-3683 produces pink aerial mycelium. In our side-by-side comparisons, both *A. fulva* Ferm-P3683 and *A. fulva* subsp. *indica* SCC 1840, form a white, yellowish white or ivory aerial mycelium. *A. fulva* subsp. *uruguayensis* SCC 1778, ATCC 53713 tends to form very sparse aerial mycelia, but when visible, the aerial mycelia are white. The aerial mycelium of all three organisms produce chains of smooth-walled spores which are arranged in tightly appressed spirals forming distinct pseudosporangia. All three microorganisms form only yellow-brown diffusible pigments.

*A. fulva* Ferm-P3683 differs from the micro-organism of this invention, SCC 1778, in that *A. fulva* Ferm-P3683 fails to produce acid from i-inositol and β-methyl-d-glucopyranoside, does form allantoinase and grows in the presence of 50 μg/ml of neomycin. The microorganism of this invention, SCC 1778, is therefore considered to represent a subspecies of *A. fulva*.

The microorganism of this invention, SCC 1778, ATCC 53713 produces a less abundant aerial mycelium on a wider variety of media than does *A. fulva* subsp. *indica* ATCC 53715. *A. fulva* subsp. *indica* also produces acid from L-arabinose and hydrolyses urea and hippurate while the microorganism of this invention, SCC 1778, ATCC 53713 does not. SCC 1778 is considered therefore to be a distinct new subspecies of *A. fulva* designated *A. fulva* subsp. *urugurayensis* SCC 1778, ATCC 53713.

TABLE 1

Macroscopic Appearance of *Actinomadura fulva* subsp. uruguayensis SCC 1778, ATCC 53713 on various descriptive media[a]

| MEDIUM | RESULT |
| --- | --- |
| Yeast Extract-<br>Malt Extract Agar (ISP 2) | G: good<br>AM: none to sparse, white<br>SC: moderate to numerous<br>DFP: absent<br>SMP: brown |
| Oatmeal Agar<br>(ISP 3) | G: fair<br>AM: not visible<br>SC: sparse to moderate<br>DFP: pale yellow-brown<br>SMP: translucent to yellow-brown<br>(CHM-2fb, bamboo, buffer) |
| Inorganic Salts-<br>Starch Agar<br>(ISP 4) | G: fair<br>AM: not visible<br>SC: sparse to moderate<br>DFP: absent<br>SMP: translucent to yellow-brown |
| Glycerol-Asparagine<br>Agar<br>(ISP 5) | G: fair to good<br>AM: not visible<br>SC: sparse to moderate<br>DFP: absent<br>SMP: translucent to yellow-brown |
| Peptone-Yeast Extract-<br>Iron Agar<br>(ISP 6) | G: fair to good<br>AM: not visible<br>SC: absent<br>DFP: pale yellow-brown<br>SMP: yellow-brown to brown<br>(CHM 4ng, lt. brown, maple) |
| AV Agar | G: fair<br>AM: not visible<br>SC: absent<br>DFP: absent<br>SMP: yellow-brown to brown |
| Gauze's Mineral<br>Agar I | G: fair<br>AM: not visible<br>SC: absent<br>DFP: absent<br>SMP: ivory (CHM 2db) to pale yellow-brown |
| ATTC Medium 172 | G: excellent<br>AM: not visible<br>SC: absent<br>DFP: yellow-brown<br>SMP: brown (CHM 4ng, Lt. brown, maple) |
| Czapek-Sucrose<br>Agar | G: poor<br>AM: not visible<br>SC: sparse to moderate<br>DFP: absent<br>SMP: translucent, off-white to pale yellow-brown |
| Glucose-Yeast Extract<br>Agar | G: excellent<br>AM: not visible<br>SC: absent<br>DFP: pale yellow-brown<br>SMP: yellow-brown to brown<br>(CHM 4pr, oak brown) |

[a]G = growth; AM = aerial mycellum; SC = spore chain;
DFP = diffusible pigment;
SMP = substrate mycellum pigmentation

FERMENTATION OF THE MICROORGANISM

The antimicrobial complex 510 of this invention is produced when the elaborating microorganism, *Actinomadura fulva* subsp. *uruguayensis* SCC 1778, ATCC 53713 is grown in an aqueous nutrient medium under submerged aerobic conditions at a temperature of about 27° C. to 40° C., preferably at from 27° C. to 35° C., and at a pH of from about 6.5 to 8.0 with agitation until substantial antimicrobial activity is imparted to the medium. Temperature studies indicate that the organism grows rapidly at about 30° C. Therefore, the fermentation is preferably conducted employing a single temperature pattern of 30° C. for a period of about 24 to about 96 hours preferably about 90 hours. The fermentation is generally conducted from about 3 to 7 days, preferably for about 4 days (90 hrs.).

To determine when peak antimicrobial production has been reached, samples of the fermentation broth were assayed every 24 hours (starting at 48 hrs.) for antimicrobial content by bioassay of the whole broth against *Staphylococcus aureus* ATCC 209P (pH 8.0), *Escherichia coli* ATCC 10536 (pH 8.0) and *Candida albicans* Wisconsin. The growth of the organism (packed cell volume), pH and dissolved oxygen levels are determined either intermittently or continuously.

As nutrient medium, there is employed any suitable medium containing a source of carbon, for example an assimilable carbohydrate, and a source of nitrogen, for example an assimilable nitrogenous or proteinaceous material and various mineral salts.

The medium employed for the fermentation contained beet extract (an enzymatic hydrolysate of casein) and insoluble starch as the major sources of nitrogen and carbon, respectively. Under these conditions, the microorganism, SCC 1778, produced antimicrobial complex 510 containing at least one biologically active component as determined by bioautography against both *S. aureus*, *E. coli* and *C. abicans* of the complex after development of a thin layer chromatography plate in 2:2:1 (v/v/v) chloroform: methanol:pH 3.5 acetate buffer.

The foregoing media are exemplary of the nutrients utilized by *Actinomadura fulva* subsp. *uruguayensis* to produce antimicrobial complex 510. However, it is obvious to those trained in the fermentation science that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from 6.5 to 8.0, a pH of from 6.5 to 7.5 being preferred. Prior to sterilization, the pH of the medium is usually adjusted to 7.0.

The fermentation was initiated by addition of the inoculum to the broth. Generally, inoculum volume is 3.0% of total broth volume. The inoculum is prepared by addition of a sample of the frozen whole broth to an appropriate medium. A particularly preferred inoculum preparation medium comprises beef extract, 0.3%; tryptone, 0.5%; cerelose, 0.1% potato starch, 2.4%; yeast extract, 0.5%; and calcium carbonate, 0.2% (all percents by weight). The inoculum stage of the fermentation usually requires from 24 to 120 hours with 2 to 4 days preferred and is generally conducted at about 30° C. with agitation. Agitation and a positive air flow, generally about 3.5 L/min. a 90 hour incubation period and a temperature of about 30° C. are employed during the fermentations medium comprises cottonseed flower, 1.0%; peptone 0.1%; cerelose, 5.0%; cornsteep liquor, 0.5 vol. %; arabinose, 0.5%, $MgCl_2.6H_2O$, 0.05% and 0.1 vol. % of each of: (1) a 5 wt % solution of $ZnSO_4 \cdot 7H_2O$; and (2) a 1.4 wt % solution of $FeSO_4 \cdot 7H_2O$. The pH of the solution is adjusted to 7 prior to the addition of mineral salts. An antifoam agent such as Antifoam AF-1 (Dow Corning) is added, if necessary, to the fermentors to control foam.

ISOLATION AND PURIFICATION OF THE ANTIMICROBIAL COMPLEX 510

The antimicrobial complex 510 of this invention contains a complex mixture of antimicrobials, including as the major components the three compounds represented by formula 1, macrolactam monosaccharides along with a fourth macrolactam monosaccharide of formula 2 as well as several minor components. The antimicrobial complex 510 of this invention is isolated by extraction of the whole fermentation broth at a pH of 9.5 with ethyl acetate. The ethyl acetate extracts were shaken with water at pH of 2. The aqueous layer was extracted with n-butanol. The n-butanol extract is washed, dried, concentrated, dissolved in methanol; the so formed mixture is added to an ether:hexane mixture. The so-formed precipitate is the antimicrobial complex 510 of this invention which exhibits antifungal activity against fungi such as Candida sp. and antibacterial activity against Gram positive and gram negative bacteria.

ISOLATION AND PURIFICATION OF THE COMPOUNDS OF THIS INVENTION

The major antimicrobial components of the antimicrobial complex 510 were isolated as individual components by passage of the antimicrobial complex 510 through a partition chromatography column, Sephadex LH-20 (Pharmecia), followed by elution with methanol, followed by droplet countercurrent chromatography (DCC) on a column using as the eluate a mixture of chloroform:methanol:water (7:13:8, v/v/v).

Preparative reverse phase chromatography on MCI CHP 20P gel (Mitsubishi) using a linear methanol gradient in acid on the antimicrobial complex 510 can also be used to obtain a separation of the three novel macrolactam monosaccharides of formula 1 and of the known macrolactam monosaccharide of formula 2.

The compounds represented by formula 1 and 2 were analyzed by high resolution Fast Atom Bombardment-Mass Spectral (FAB-MS) and carbon-13 NMR. The physicochemical data for the compounds represented by formulas 1 and 2 are shown in Tables II, III and IV.

TABLE II

High Resolution FAB-Mass Spectral Data for the Compounds of Formulas 1 and 2

| Compound | Calc. | Found | Δ PPM | m/z |
|---|---|---|---|---|
| Formula 1 ($R_1 = R_2 = R_3 = H$) | 415.3172 | 415.3162 | 2 | 252,164,146 |
| Formula 1 $R_1 = R_2 = H$, $R_3 = CH_3$ | 429.3328 | 429.3333 | 1 | 266,164,146 |
| Formula 1 $R_1 = H; R_2 = R_3 = CH_3$ | 443.3485 | 443.3353 | 7 | 280,164,146 |
| Formula 2 | 457.3641 | 457.3674 | 3 | 294,164,146 |

Based on the high resolution FAB-MS data in Table II, the molecular formulas for compounds of formulas 1 and 2 were determined and are given in Table III.

TABLE III

Molecular Formulas of Compounds of Formulas 1 and 2

| Compound | Molecular Formula |
|---|---|
| Formula 1 $R_1 = R_2 = R_3 = H$ | $C_{22}H_{42}N_2O_5$ |
| Formula 1 $R_1 = R_2 = H$; $R_3 = CH_3$ | $C_{23}H_{44}N_2O_5$ |
| Formula 1 $R_1 = H; R_2 = R_3 = CH_3$ | $C_{24}H_{46}N_2O_5$ |
| Formula 2 | $C_{25}H_{48}N_2O_5$ |

We determined that the C-13 NMR (fully decoupled and INEPT) spectra of the compounds of formula 1 and the C-13 NMR for the compound of formula 2; the data are listed in Table IV.

TABLE IV

C-13 NMR Data for Compounds of Formulas 1 and 2

| | Carbon | Formula 1 $R_1 = R_2 = R_3 = H$ | Formula 1 $R_1 = R_2 = H$; $R_3 = CH_3$ | Formula 1 $R_1 = H$; $R_2 = R_3 = CH_3$ | Formula 2 |
|---|---|---|---|---|---|
| | 2 | 38.9 | 39.1 | 39.8 | 39.2 |
| | 3 | 28.5 | 28.8 | 28.3 | 28.1 |
| | 4 | 29.9 | 29.6 | 22.4 | 25.5 |
| | 5 | 36.1 | 36.4 | 42.0 | 41.2 |
| $CH_2$ | 5' | — | — | 22.0 | 21.5 |
| $CH_3$ | 5" | 17.3 | 17.4 | 9.2 | 8.9 |
| | 6 | 79.5 | 79.9 | 78.3 | 76.9 |
| | 7 | 20.4 | 20.6 | 22.0 | 21.7 |
| | 8 | 25.8 | 26.0 | 26.2 | 22.7 |
| | 9 | 31.1 | 29.9 | 28.6 | 39.0 |
| $CH_2$ | 9' | — | — | — | 27.6 |
| $CH_3$ | 9" | 18.5 | 18.6 | 18.9 | 12.6 |
| | 10 | 35.4 | 35.8 | 36.0 | 32.5 |
| | 11 | 24.5 | 23.2 | 23.5 | 25.5 |
| | 12 | 34.5 | 32.7 | 33.2 | 33.9 |
| | 13 | 42.6 | 51.7 | 49.8 | 50.7 |
| $CH_2$ | 13' | — | 27.6 | 26.2 | 26.9 |
| $CH_3$ | 13" | 13.8 | 12.6 | 12.9 | 12.3 |
| | 14 | 178.6 | 178.9 | 179.0 | 178.2 |
| | 1' | 96.1 | 96.4 | 98.0 | 97.5 |
| | 2' | 70.7 | 70.5 | 70.4 | 72.9 |
| | 3' | 54.3 | 54.3 | 55.2 | 53.8 |
| | 4' | 69.3 | 69.6 | 70.7 | 71.0 |
| | 5' | 68.4 | 69.6 | 69.9 | 69.8 |
| | 6' | 17.2 | 17.3 | 17.7 | 17.7 |

The compound of formula 2 is shown below

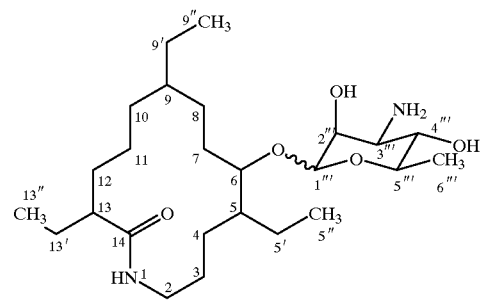

2

The physiochemical data in Tables II, III and IV indicate the compounds of formulas 1 and 2 are fourteen membered macrocyclic lactams and have the same amino sugar, mycosamine, and such data are consistent with the structures for the macrolactam monosaccharides represented by formula 1.

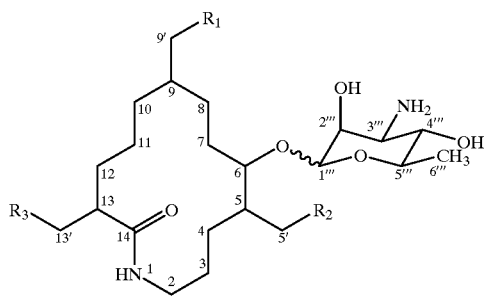

(a): $R_1 = R_2 = R_3 = H$; (b): $R_1 = R_2 = H, R_3 = CH_3$; (c): $R_1 = H, R_2 = R_3 = CH_3$

THE BIOLOGICAL ACTIVITY OF THE ANTIMICROBIAL COMPLEX, THE COMPOUND OF FORMULA 1

The antimicrobial complex 510 of this invention exhibits both antifungal activity and antibacterial activity in vitro against Gram positive and Gram negative microorganisms.

The three compounds represented by formula 1, isolated from the antimcrobial complex 510, exhibit in vitro antifungal activity in a Sabouraud dextrose broth ("SDB") medium against seven species of Candida and six species of dermatophytes and antifungal activity against seven species of Candida in Eagles Minimum Essential Medium ("EMEM").

The in vitro antifungal data on the compounds of formula 1 are presented in Table V.

TABLE V

In vitro Antifungal Data on the Compounds of Formula 1

| | | Compounds of Formula 1 | | |
|---|---|---|---|---|
| Organism (No. of Strains) | Medium | (a) | (b) | (c) |
| Candida (7) | SDB | 29 | 18 | 4.4 |
| Dermatophytes (6) | SDB | ≧114 | ≧128 | ≧57 |
| Candida (7) | EMEM | ≧105 | ≧71 | 24 | a) $R_1 = R_2 = R_3 = H$
b) $R_1 = R_2 = H; R_3 = CH_3$
c) $R_3 = R_2 = CH_3; R_1 = H$

PHARMACEUTICAL COMPOSITIONS

This invention also contemplates antimicrobially effective pharmaceutical compositions comprising an antimicrobially effective amount of a compound of formula 1 or pharmaceutically acceptable salts thereof in admixture with a pharmaceutically acceptable, non-toxic carrier adapted for topical, oral or parenteral use.

The preferred pharmaceutically acceptable salts are non-toxic acid addition salts formed by adding to the compounds of the present invention about a stoichiometric amount of a mineral acid, such as HCl, HBr, $H_2SO_4$ or $H_3PO_4$, or of an organic acid, such as acetic, propionic, valeric, oleic, palmitic, stearic, lauric, benzoic, lactic, para-toluenesulfonic, methane sulfonic, citric, maleic, fumaric, succinic and the like.

The topical, oral and parenteral dosage forms may be prepared according to procedures well known in the art, and may contain a variety of ingredients.

In the case of topical formulations, e.g., ointments, creams, lotions, powders, tablets, pessaries or sprays, the formulation will contain about 0.1 to 10 grams of a compound of formula 1 per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and may contain salts or glucose to make the solution isotonic.

In general, the dosage of compound of formula 1 administered to combat a given microbial infection is similar to the dosage requirements of the present commercial products miconazole, clotrimazole, and ketoconazole.

In general, the topical dosage range of the compound of formula 1 is from about 0.1% to about 10% by weight of a particular pharmaceutical composition formulated in single or divided doses, with the preferred range being about 0.5% to about 4% and with the most preferred range being about 1% to about 2%.

In general, the oral dosage for humans of the compound of formula 1 administered to combat a given microbial infection ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans of the compound of formula 1 administered to combat a given microbial infection ranges for about 0.1 mg per kilogram of body weight per day, to about 20 mg per kilogram of body weight per day, in single or divided doses, with about 1 mg per kilogram of body weight per day being preferred.

It will be appreciated that the actual preferred dosages of the compounds of this invention or pharmaceutically acceptable salts thereof will vary according to the particular compound chosen, the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

The following examples illustrate the invention:

EXAMPLE 1

Preparation of the Antimicrobial Complex 510 of This Invention

A. Inoculum Preparation

1) Initial Stage

Prepare a 250 mL Erlemneyer flask with 70 mL of the following germination medium:

| | |
|---|---|
| Beef Extract | 3 g |
| Tryptone | 5 g |
| Yeast Extract | 5 g |
| Cerelose | 1 g |
| Potato Starch | 24 g |
| Calcium Carbonate | 2 g |
| Tap Water | 1000 mL |
| AF-1* | 1 mL |

*AF-1 is an antifoam agent available from Dow Corning Corp., Midland, MI 48641.

Sterilize the broth and after cooling, add 3.5 mL of a frozen whole broth sample of the microorganism of this invention from a previously prepared inoculum to each flask broth. Incubate at 30° C. with continual agitation at 300 rpm for 48 hours.

2) Second Stage

Transfer 25 mL of the first stage germination broth to each of twenty 2-liter Erlenmeyer flasks, each containing 500 mL of the same germination medium and which had been previously pH adjusted and sterilized. Incubate at 30° C. with continual agitation at 300 rpm for 48 hours.

B. Fermentation

In a 150 L fermentor, add 100 L of the following medium:

| | g/L |
|---|---|
| Cotton Seed flour | 10.0 |
| Peptones | 1.0 |
| Consteep Liquor | 5.0 ml |
| Arabinose | 5.0 |
| Cerelose | 5.0 |
| $MgCl_2 \cdot 6H_2O$ | 0.5 |
| $ZnSO_4 \cdot 7H_2O$ (5% Solution) | 1.0 ml |
| $FeSO_4 \cdot 7H_2O$ (1.4% Solution) | 1.0 ml |
| Antifoam (AF-1 Dow Corning) | 1.0 ml |

Adjust the pH of the medium to 7.0 and add the inorganic salts and then sterilize the medium. Inoculate the fermentation medium with 5 volume % of the second stage inoculum preparation of Step A. Incubate the fermentation mixture at 30° C. with 1.6 cubic feet per minute of air flow and 350 rpm agitation for about 90 hours. Use a 150 L fermentor to produce about 130 L of a whole broth containing antimicrobial complex 510.

C. Isolation

Option #1

Extract 310 L of the whole fermentation broth at a pH of 9.5 produced in accordance with the fermentation procedure hereinabove with two 500 L volumes of ethyl acetate. The ethyl acetate extracts were concentrated in vacuo to 10 L and extracted with 5 L of water at a pH of 2. The aqueous extracts were adjusted to pH 8.5 and were reextracted with 5 L of n-butanol. The combined n-butanol extracts were concentrated to 1 L and washed with 2 L of water three times. Concentrate the washed n-butanol extract to 1 L and dissolve the concentrate in 3 L of methanol. Add to the so-formed methanol solution, 3.5 L of diethylether:hexane (1:1, v/v) to produce 850 mg of crude antimicrobial complex 510 as a gum.

The crude antimicrobial complex 510 was purified by use of Sephadex LH 20 in methanol. Chromatography was carried out using a 3 cm(diameter)×60 cm length column, eluting at 2.5 ml/min, collecting five mL fractions. Fractions 24–45 were combined and concentrated in vacuo to yield 300 mg pf crude cpmplex 510.

The compounds of formula 1 were obtained as three substantially chemically pure compounds by use of droplet counter current chromatography using chloroform:methanol:water (7:13:8, v/v/v) mixture. The physiochemical data for the compounds of formula 1 are summarized in Tables II, III and IV.

Option #2

The whole fermentation broth (300 L) was adjusted to pH 2 with addition of acid, and stirring, then readjusted to pH 9.5 with addition of base. Extract 300 L of the whole broth at a pH of 9.5 with two 500 L volumes of ethyl acetate. The ethyl acetate extracts were concentrated in vacuo to approximately 10 L and extracted with 5 L of water at a pH of 2. The aqueous extracts were adjusted to pH 8.5 and reextracted with 5 L of n-butanol. The combined n-butanol extracts were concentrated to approximately 1 L, and then poured into 3.5 L of diethyl ether with vigorous stirring. The crude antimirobial complex 510 (8 g) precipitated as a gum.

The crude antimicrobial complex 510 was purified by chromatography on a MCI CHP20P gel (75–150μ) using a column (1 3/16" diameter and 48" length) eluting with a linear gradient of 30% aqueous methanol to 90% aqueous methanol in $H_2O$ adjusted to pH 2 with acetic acid. The flow rate was 2.5 mL/min and 20 mL fractions were collected. Fractions 210–224 contained the compound of formula 1, ($R_1=R_2=R_3=H$) (15 mg), fraction 238–248 contained the compound of formula 1, ($R_1=R_2,H$, $R_3=CH_3$) (60 mg) and fractions 249–276 contained the compound of formula 1, ($R_1=H$, $R_2=R_3=CH_3$) (112 mg).

What is claimed is:

1. A compound represented by the formula 1:

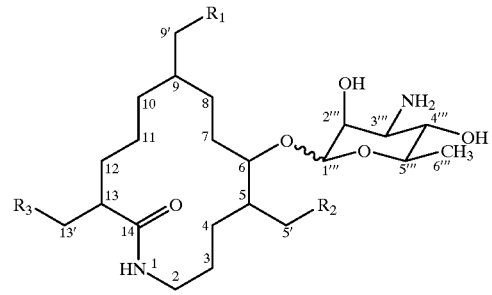

wherein $R_1=R_2=R_3=H$; or $R_1=R_2=H$ and $R_3=CH_3$; or $R_1=H$ and $R_2=R_3=CH_3$;

in chemically pure form, or a pharmaceutically acceptable salt thereof.

2. The compound of claim 1 wherein $R_1=R_2=R_3=H$.

3. The compound of claim 1 wherein $R_1=R_2=H$ and $R_3=CH_3$.

4. The compound of claim 1 wherein $R_1=H$ and $R_2=R_3=CH_3$.

5. A pharmaceutical composition comprising an antimicrobially effective amount of the compound of claim 1 and a pharmaceutically acceptable carrier or diluent.

6. The pharmaceutical composition of claim 5 suitable for parenteral administration.

7. The pharmaceutical composition of claim 5 suitable for topical administration.

8. The pharmaceutical composition of claim 5 suitable for oral administration.

9. A method for treating a bacterial infection in a host comprising administering to said host an antibacterially effective amount of the compound of claim 1 or a pharmaceutical composition thereof.

10. The method of claim 9 wherein the route of administration is parenteral.

11. The method of claim 9 wherein the route of administration is topical.

12. The method of claim 9 wherein the route of administration is oral.

* * * * *